United States Patent [19]
Niederhauser et al.

[11] Patent Number: 4,663,354
[45] Date of Patent: May 5, 1987

[54] USE OF ETILEFRIN AND ETILEFRIN PIVALATE IN THE LONG TERM TREATMENT OF CIRCULATORY DISORDERS NOT DUE TO HYPOTONIA

[75] Inventors: Alois Niederhauser, Neukirchen am Teisenberg; Klaus Seibel, Gräfelfing, both of Fed. Rep. of Germany

[73] Assignee: Klinge Pharma GmbH, Fed. Rep. of Germany

[21] Appl. No.: 724,979

[22] Filed: Apr. 19, 1985

[30] Foreign Application Priority Data

Apr. 26, 1984 [DE] Fed. Rep. of Germany ....... 3415575

[51] Int. Cl.$^4$ ............................................. A61K 31/135
[52] U.S. Cl. .................................................... 514/649
[58] Field of Search ......................................... 514/649

[56] References Cited

U.S. PATENT DOCUMENTS 4,374,841  2/1983  Descamps et al. .................. 514/351

OTHER PUBLICATIONS

Textbook of Medicine; Cecil, 16th Ed. (1982), p. 2120.
Medical Botany (1977), Walter H. Lewis, pp. 189–190.
Chemical Abstracts, vol. 83 (1975), #37898p; Coleman et al.

Primary Examiner—Leonard Schenkman
Assistant Examiner—Joseph A. Lipovsky
Attorney, Agent, or Firm—Burns, Doane, Swecker & Mathis

[57] ABSTRACT

The use of etilefrin or etilefrin pivalate in the long term treatment of circulatory disorders not due to hypotonia, such as for example peripheral arterial stenoses, leads surprisingly to a continuous stable rise in systolic blood pressure and blood pressure amplitude and an improved cardiac output, without affecting the diastolic blood pressure or the cardiac frequency. The pharmaceutical effect is enhanced by using etilefrin in combination with an extract of horse chestnut seeds in a long term treatment.

3 Claims, 2 Drawing Figures

HEART RATE DURING A SIX-MONTH TREATMENT WITH ETILEFRIN PIVALATE (20 MG P.O. DAILY). AFTER SIX MONTHS THE MEDICATION HAS BEEN WITHDRAWN (↑). MEANS ± STANDARD DEVIATION.

USE OF ETILEFRIN AND ETILEFRIN PIVALATE IN THE LONG TERM TREATMENT OF CIRCULATORY DISORDERS NOT DUE TO HYPOTONIA

BACKGROUND OF THE INVENTION

The invention relates to the use of etilefrin and etilefrin pivalate in the treatment of circulation disorders.

The sympathomimetic drug etilefrin has been used heretofore as a rapid acting medicine in circulation disorders, in particular in hypotonia and orthostatic hypotension and is described in standard pharmacological works exclusively as a means to increase blood pressure. The increase in blood pressure is effected by the known vasoconstrictory action of the substance. Etilefrin has in addition to its vasoconstrictory action, also a stimulating effect on the heart, which, however, is manifested only by a very slight increase in the cardiac output. In the case of the oral or parenteral administration of such sympathomimetic agents, in addition to an increase in blood pressure, simultaneously an undesirable acceleration of cardiac frequency is observed, in particular if an attempt is made to obtain a relevant rise of the cardiac output by the administration of higher doses of the active ingredient.

In view of the short half-life of 2.2 hours for the elimination of etilefrin from the blood circulation, no stable, increased blood pressure amplitude can be obtained in the patient even with the administration of higher doses, even though this is a necessary requirement in the long term elimination of circulatory disorders and their symptoms. If the circulation disorders are due to cerebral or peripheral arterial stenosis, such as in the case of arteriosclerosis or to cerebral vasoconstriction as in migraine, the application of etilefrin may even be inappropriate in view of its vasoconstrictory effect, as a further reduction in the lumen of peripheral vessels would necessarily lead to a further deterioration of circulation.

SUMMARY OF THE INVENTION

The present invention is a method for the long term treatment of a mammal having a circulatory disorder not due to hypotonia. In the method, a cardiac output increasing effective amount of etilefrin or etilefrin pivalate is administered. In a preferred embodiment, the etilefrin or etilefrin pivalate is combined with horse chestnut seed extract. The invention also includes a pharmaceutical preparation.

DETAILED DESCRIPTION OF THE INVENTION

Figure 1:
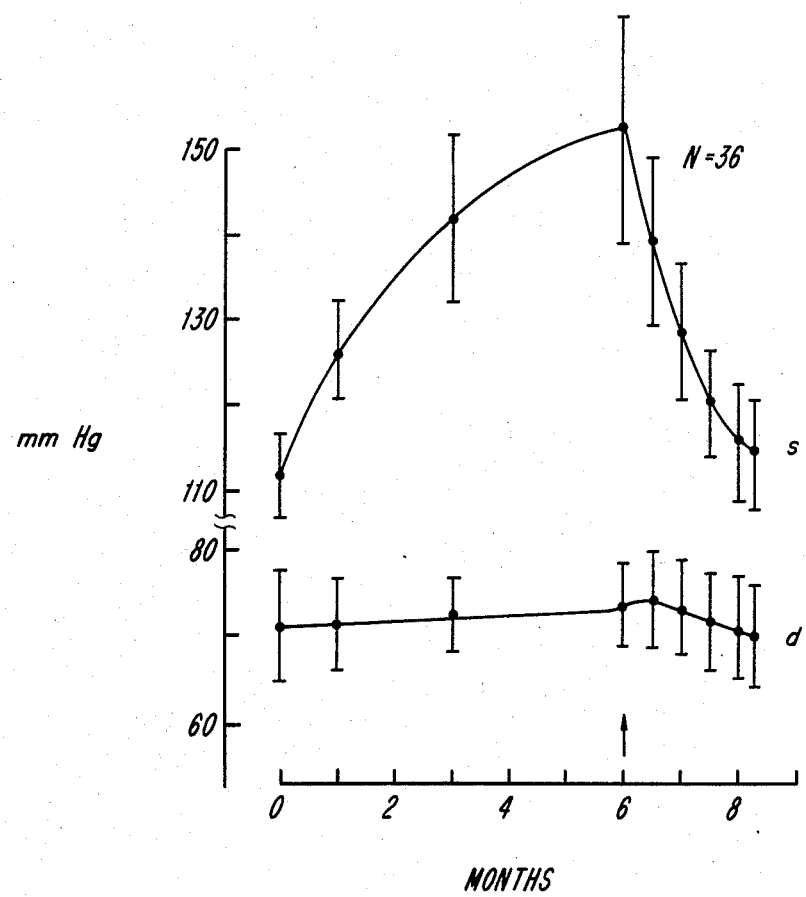
Figure 2:
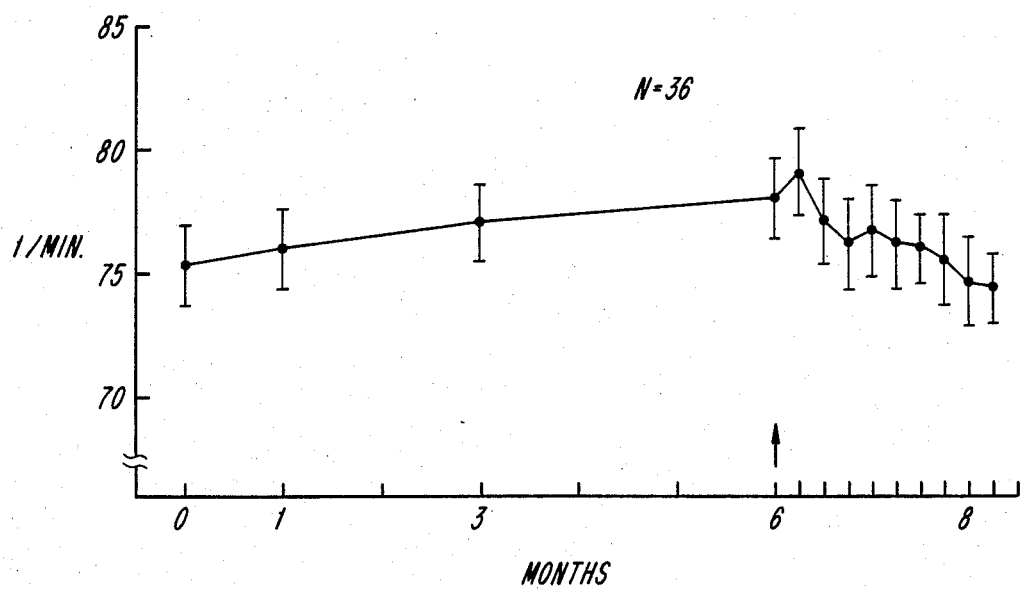

It has now been discovered surprisingly that with an extended regular use of low doses of etilefrin and etilefrin pivalate, the cardiac output may be appreciably and constantly increased. In a long term tolerance study of 6 months most of the patients were treated with a dose as low as 20 mg of etilefrin pivalate per day corresponding to 14.4 mg etilefrin. As a consequence of this medication the systolic blood pressure and the pressure amplitude were continuously increased, while the diastolic blood pressure and the cardiac frequency remained nearly constant (FIG. 1 and 2). It is especially remarkable and surprising in the process that the blood pressure amplitude increased continuously during the 6 months' treatment phase, even though in view of the short half-life of etilefrin of 2.2 hours an accumulation of the active ingredient in the blood is inconceivable. It must be mentioned in this context that after application of etilefrin pivalate only etilefrin is found in the blood indicating that etilefrin pivalate is completely split etilefrin and pivalinic acid during absorption. The increase in blood pressure amplitude and systolic blood pressure must be particularly emphasized in view of the therapeutic objective of increasing the cardiac stroke volume in case of cerebral and peripheral arterial stenosis or vasoconstriction. As indicated by the constant diastolic blood pressure, there is no increase in the peripheral resistance during the treatment phase with the dosage chosen, in spite of the vasoconstrictory effect of etilefrin, so that surprisingly no undesirable vasoconstriction takes place in the long term treatment of circulatory disorders.

At the same time, equal results were obtained with etilefrin and etilefrin pivalate in a comparative study. In this long term treatment of 4 weeks and a dosage of twice daily of 10.82 mg etilefrin (sold under the trademark EFFORTIL ®) and 15 mg etilefrin pivalate, corresponding to the administration of $5 \times 10^{-5}$ mole of the active ingredient, the blood pressure amplitude rose continuously and considerably, whereby the diastolic blood pressure and heart rate remained nearly unchanged. At the termination of the treatment period, the blood pressure amplitude while standing, was higher with etilefrin pivalate and nearly as high with etilefrin as when lying down before treatment.

Even though the mechanism of action in the case of treatment according to the invention has not been elucidated, an obvious advantage is obtained in the treatment of the aforementioned circulatory disorders, as the time of the day of the administration of the medication is of little importance for the stroke volume increasing effect. The therapeutic protection of the patient is given not only during the night, but also in the morning when the tendency to orthostatic malfunctioning is the greatest. It is remarkable further that the effect of the two substances on the blood pressure amplitude is independent of the position of the body of the patient, i.e. it is present to the same extent while standing up or lying down.

The use of etilefrin or etilefrin pivalate thus makes it possible for the first time to obtain a lasting increase in cardiac output over an extended period of time, being able thereby to treat arterial stenoses, circulatory disorders of the retina, cerebrovascular insufficiencies, migraine, and also aging hearts having a reduced cardiac output, without having to accept the risk of undesirable vasoconstriction and increased cardiac frequency.

It has further been discovered surprisingly that the effect of etilefrin may be enhanced even more by administering an extract of horse chestnut seeds simultaneously with the etilefrin treatment. As shown by investigations using a combined product, the blood pressure amplitude is further increased. In this case again, the blood pressure amplitude at the end of the fourth week of treatment with the combination product is the same while standing, as when lying down prior to the treatment.

The invention will become more apparent from the description below of a study effected during the treatment.

To objectively determine the effect of the substances administered one to two days prior to the treatment and on the seventh, fourteenth and twenty-eighth day a modified Schellong test was conducted. Blood pressure and cardiac frequency were recorded uniformly in the morning at the same hour using Bosomat type automatic blood pressure recording instruments. This assured the objectivity of the blood pressure measurements in addition to the double blind method. Measurements were effected lying down 15 and 1 minutes prior to rising and 1, 3, 5, 7 and 9 minutes after rising. Nocturnal rest of several hours always preceded the recording of the first measured value. On the days of the measurements, the morning dose of the product was taken immediately after determination of the lying-down value 15 minutes prior to rising.

The statistical evaluation was performed by using the Dunn-Rankin, the Mann-Whitney-Wilcoxon and the Friedmann tests.

The objective evaluation of the course of treatment centered on the standing test, which provided a good insight into the conditions of circulatory regulation.

on all of the measuring days being significantly different (p <0.01). Thus for example while using etilefrin pivalate an increase of 107.3 mm Hg to 114.3 was obtained on the 7th day, to 119.1 on the 14th and 124.7 mm Hg on the 28th day of the treatment (measured always 15 minutes before rising) and in the etilefrin group from 109.1 mm Hg prior to the onset of the treatment to 119.4 mm Hg on the 28th day of treatment. It is seen from the 14th day of treatment on that etilefrin pivalate is more effective with respect to the systolic blood pressure than etilefrin.

The standing tests show in essence a similar rise in the systolic blood pressure under the effect of both substances. This indicates that the blood pressure effect generated by the two sympathomimetic agents when the body is in the horizontal position, is retained while standing up.

Table 2 shows the values measured for the diastolic blood pressure:

TABLE 2

Diastolic blood pressure at the beginning and during treatment with etilefrin pivalate and etilefrin (mm Hg: x ± s)

| | Control Day | | | | | | | |
|---|---|---|---|---|---|---|---|---|
| | Etilefrin pivalate | | | | Etilefrin | | | |
| Time | Before Treatment | 7th Day of Treatment | 14th Day of Treatment | 28th Day of Treatment | Before Treatment | 7th Day of Treatment | 14th Day of Treatment | 28th Day of Treatment |
| Lying Down/ 15 min. before rising | 70.0 ± 3.8 | 71.7 ± 4.4 | 72.5 ± 4.4 | 73.1 ± 3.4 | 69.7 ± 4.9 | 70.7 ± 4.6 | 71.1 ± 3.8 | 72.2 ± 3.6 |
| Lying Down/ 1 min. before rising | 69.5 ± 3.6 | 71.5 ± 5.0 | 72.3 ± 4.6 | 72.7 ± 2.9 | 69.1 ± 4.8 | 69.7 ± 4.7 | 70.2 ± 4.0 | 71.3 ± 3.3 |
| After standing for 1 minute | 76.1 ± 6.4 | 77.3 ± 4.8 | 78.8 ± 5.8 | 79.5 ± 4.7 | 75.2 ± 5.4 | 76.1 ± 5.3 | 76.1 ± 5.0 | 76.9 ± 4.4 |
| Standing for 3 minutes | 77.9 ± 8.1 | 79.1 ± 5.5 | 79.8 ± 6.1 | 79.8 ± 4.5 | 76.3 ± 5.7 | 77.4 ± 5.9 | 76.7 ± 5.4 | 78.1 ± 4.9 |
| Standing for 5 minutes | 77.9 ± 7.2 | 79.9 ± 5.7 | 79.8 ± 5.8 | 79.9 ± 4.9 | 77.3 ± 5.8 | 77.7 ± 5.9 | 77.5 ± 5.7 | 77.5 ± 4.7 |
| Standing for 7 minutes | 78.1 ± 7.2 | 79.5 ± 5.9 | 80.1 ± 6.1 | 80.1 ± 4.5 | 76.9 ± 5.8 | 77.5 ± 5.8 | 77.4 ± 5.9 | 78.1 ± 5.4 |
| Standing for 9 minutes | 77.6 ± 6.9 | 79.7 ± 5.7 | 80.2 ± 6.0 | 79.5 ± 4.5 | 77.2 ± 6.0 | 77.9 ± 5.7 | 78.0 ± 5.2 | 77.7 ± 4.7 |

The behavior of the blood pressure and cardiac frequency during the 4-week treatment phase may be seen from the values of the seven measuring times (with standard deviation) in Tables 1 to 4. The values are the means calculated from thirty individual values of each group of patients. In the course of the statistical evaluation, the variation of the mean values when lying down, 15 minutes before rising, were always examined between two successive measuring days, with the application of the Dunn-Rankin test. The significance of differences in the effect of etilefrin and etilefrin pivalate was examined by the Mann-Whitney-Wilcoxon test.

The following results may be derived from the tables for the individual parameters:

The most important effect seen in this Table is that neither of the two active substances causes a rise in the diastolic blood pressure, and that therefore there is no indication of an increase in the peripheral resistance and thus of an undesirable vasoconstriction. Here there is only a slight rise from 70.0 to 73.1 mm Hg in the horizontal position within the 28 treatment days when using etilefrin pivalate, and from 69.7 to 72.2 mm Hg with etilefrin. The increases in the vertical position are similarly low.

As seen from Table 3, the behavior of the systolic and diastolic blood pressure is paralleled in the course of the treatment of the two patient groups from measuring day to measuring day by a significant increase in the blood

TABLE 1

Systolic blood pressure at the beginning and during the treatment with etilefrin pivalate and etilefrin (mm Hg: x ± s)

| | Control Day | | | | | | | |
|---|---|---|---|---|---|---|---|---|
| | Etilefrin pivalate | | | | Etilefrin | | | |
| Time | Before Treatment | 7th Day of Treatment | 14th Day of Treatment | 28th Day of Treatment | Before Treatment | 7th Day of Treatment | 14th Day of Treatment | 28th Day of Treatment |
| Lying Down/ 15 min. before rising | 107.3 ± 4.7 | 114.3 ± 6.7 | 119.1 ± 7.7 | 124.7 ± 9.0 | 109.1 ± 6.1 | 112.4 ± 5.7 | 115.2 ± 6.3 | 119.4 ± 6.2 |
| Lying Down/ 1 min. before rising | 106.9 ± 4.4 | 114.7 ± 6.4 | 121.1 ± 8.0 | 126.7 ± 9.3 | 108.5 ± 5.8 | 111.3 ± 5.8 | 113.9 ± 6.3 | 118.5 ± 6.6 |
| After standing for 1 minute | 103.7 ± 6.8 | 110.3 ± 7.3 | 116.1 ± 9.0 | 121.7 ± 10.5 | 104.2 ± 6.2 | 107.3 ± 6.1 | 110.5 ± 7.5 | 114.6 ± 7.7 |
| Standing for 3 minutes | 102.7 ± 6.9 | 109.3 ± 7.8 | 114.1 ± 8.8 | 120.3 ± 10.2 | 102.9 ± 6.8 | 106.4 ± 6.4 | 108.9 ± 7.8 | 113.3 ± 8.0 |
| Standing for 5 minutes | 101.4 ± 6.9 | 107.6 ± 7.9 | 113.7 ± 8.8 | 119.2 ± 9.7 | 102.3 ± 6.8 | 105.5 ± 6.6 | 107.9 ± 8.0 | 112.5 ± 7.9 |
| Standing for 7 minutes | 101.0 ± 6.7 | 107.5 ± 8.0 | 113.7 ± 8.8 | 119.0 ± 9.7 | 101.1 ± 6.6 | 104.1 ± 6.6 | 108.3 ± 8.2 | 112.6 ± 8.3 |
| Standing for 9 minutes | 99.7 ± 6.9 | 107.1 ± 7.6 | 113.1 ± 8.1 | 118.8 ± 9.2 | 100.5 ± 6.7 | 103.9 ± 6.3 | 107.3 ± 7.6 | 112.4 ± 7.5 |

As seen in Table 1, the values recorded while lying down prior to the administration of etilefrin or etilefrin pivalate are increasing continuously during the treatment period of four weeks, with the values determined pressure amplitude. It rises under the effect of etilefrin pivalate from 37.3 mm Hg prior to the treatment to 47.2 mm Hg on the 28th treatment day and with etilefrin from 39.4 mm Hg to 45.2 mm Hg.

TABLE 3

Blood pressure amplitude at the beginning and during treatment with etilefrin pivalate and etilefrin (mm Hg: $\bar{x} \pm s$)

| | Control Day | | | | | | | |
|---|---|---|---|---|---|---|---|---|
| | Etilefrin pivalate | | | | Etilefrin | | | |
| Time | Before Treatment | 7th Day of Treatment | 14th Day of Treatment | 28th Day of Treatment | Before Treatment | 7th Day of Treatment | 14th Day of Treatment | 28th Day of Treatment |
| Lying Down/ 15 min. before rising | 37.3 ± 3.8 | 42.5 ± 4.7 | 46.5 ± 6.0 | 47.2 ± 7.0 | 39.4 ± 3.9 | 41.7 ± 3.6 | 44.1 ± 4.9 | 45.2 ± 9.3 |
| Lying Down/ 1 min. before rising | 37.3 ± 3.5 | 43.3 ± 5.1 | 48.8 ± 6.4 | 53.9 ± 8.7 | 39.4 ± 3.5 | 41.5 ± 3.8 | 43.7 ± 4.7 | 47.2 ± 6.3 |
| After standing for 1 minute | 27.6 ± 4.4 | 33.1 ± 6.1 | 37.7 ± 7.0 | 42.2 ± 10.0 | 29.0 ± 4.9 | 31.2 ± 5.3 | 34.3 ± 6.2 | 37.7 ± 6.4 |
| Standing for 3 minutes | 24.8 ± 6.0 | 30.2 ± 5.8 | 34.2 ± 7.4 | 40.5 ± 9.4 | 26.5 ± 5.2 | 29.0 ± 5.5 | 32.2 ± 6.5 | 35.2 ± 7.7 |
| Standing for 5 minutes | 23.6 ± 5.9 | 27.7 ± 6.1 | 33.9 ± 6.9 | 39.3 ± 9.0 | 24.9 ± 5.9 | 27.8 ± 5.7 | 30.4 ± 6.8 | 34.9 ± 7.6 |
| Standing for 7 minutes | 22.8 ± 6.5 | 28.0 ± 6.5 | 33.7 ± 7.7 | 38.9 ± 10.3 | 24.2 ± 5.4 | 26.6 ± 6.0 | 30.9 ± 7.2 | 34.5 ± 8.6 |
| Standing for 9 minutes | 22.1 ± 6.8 | 27.3 ± 6.1 | 33.0 ± 7.0 | 39.3 ± 9.1 | 23.3 ± 6.0 | 26.1 ± 6.3 | 29.3 ± 7.0 | 34.7 ± 7.5 |

The results according to Table 1 and Table 3 show that the systolic blood pressure and the blood pressure amplitude increase 15 minutes before rising under the effect of both substances from measuring day to measuring day. This signifies that as the last administration of a dose occurred at noon on the preceding day and in view of the short half-life of both sympathomimetic agents there is no appreciable concentration of the substances in the plasma, over the long term a clear, stable increase in systolic blood pressure and blood pressure amplitude is observed and that therefore the therapeutic efficiency of the sympathomimetic drugs is very high.

As shown by Table 4, the cardiac frequency remains nearly constant during the treatment with the slight doses of the active ingredient chosen, while there is a significant increase in cardiac output.

TABLE 4

Cardiac frequency at the beginning and during the treatment with etilefrin pivalate and etilefrin (mm Hg: $\bar{x} \pm s$)

| | Control Day | | | | | | | |
|---|---|---|---|---|---|---|---|---|
| | Etilefrin pivalate | | | | Etilefrin | | | |
| Time | Before Treatment | 7th Day of Treatment | 14th Day of Treatment | 28th Day of Treatment | Before Treatment | 7th Day of Treatment | 14th Day of Treatment | 28th Day of Treatment |
| Lying Down/ 15 min. before rising | 71.2 ± 3.4 | 71.5 ± 2.7 | 71.7 ± 2.6 | 71.9 ± 3.0 | 71.1 ± 3.6 | 71.6 ± 3.1 | 71.5 ± 2.9 | 71.3 ± 2.7 |
| Lying Down/ 1 minute before rising | 70.4 ± 3.1 | 70.8 ± 2.6 | 70.9 ± 2.9 | 71.3 ± 2.9 | 70.4 ± 3.4 | 70.6 ± 2.9 | 70.6 ± 3.0 | 70.5 ± 2.6 |
| After standing for 1 minute | 87.2 ± 6.7 | 84.5 ± 3.9 | 84.3 ± 4.8 | 83.0 ± 4.1 | 85.8 ± 4.5 | 84.2 ± 5.3 | 83.2 ± 2.9 | 81.5 ± 4.1 |
| After standing for 3 minutes | 91.5 ± 5.5 | 87.5 ± 4.3 | 86.8 ± 4.4 | 85.3 ± 4.1 | 89.3 ± 4.7 | 86.8 ± 3.6 | 85.9 ± 4.0 | 83.6 ± 4.0 |
| After standing for 5 minutes | 94.2 ± 6.7 | 89.5 ± 4.7 | 88.1 ± 5.1 | 85.5 ± 4.3 | 92.2 ± 5.6 | 88.8 ± 4.5 | 86.7 ± 4.4 | 86.3 ± 4.4 |
| After standing for 7 minutes | 94.4 ± 7.5 | 90.4 ± 6.4 | 86.7 ± 5.3 | 85.5 ± 5.0 | 92.2 ± 5.8 | 89.4 ± 6.3 | 87.0 ± 4.5 | 85.3 ± 4.9 |
| After standing for 9 minutes | 94.3 ± 8.1 | 90.3 ± 5.6 | 87.4 ± 4.4 | 84.9 ± 9.4 | 91.9 ± 5.5 | 89.2 ± 4.3 | 87.1 ± 3.5 | 84.7 ± 4.6 |

The enhanced effect of etilefrin in combination with the extract of horse chestnut seeds is demonstrated in Table 5. For this purpose, in a double blind study the blood pressure effect of a combination of horse chestnut seed extract and etilefrin (20 mg etilefrin hydrochloride and 150 mg horse chestnut seed extract, standardized to 25 mg aescinic acid) was compared with the effect of the etilefrin component and of a placebo. The subsequent treatment lasted 4 weeks.

TABLE 5

Blood pressure and blood pressure amplitude (mm Hg) during the standing experiments at the onset and the end of the treatment

| | Etilefrin and horse chestnut seed extract | | Etilefrin | | Placebo | |
|---|---|---|---|---|---|---|
| | Before Treatment | After Treatment | Before Treatment | After Treatment | Before Treatment | After Treatment |
| RR syst. Lying Down | 108.0 ± 5.5 | $123.1^x \pm 6.7^o$ | 107.3 ± 4.9 | $118.4^o \pm 7.8$ | 106.0 ± 5.6 | 106.1 ± 7.1 |
| RR syst. Standing | 101.3 ± 5.9 | $116.6^x \pm 7.0^o$ | 101.4 ± 5.3 | $112.4^o \pm 7.8$ | 98.9 ± 4.9 | 99.9 ± 4.2 |
| RR diast. Lying Down | 68.3 ± 4.6 | $71.1^o \pm 2.9$ | 69.1 ± 3.9 | $71.0^o \pm 2.7$ | 67.0 ± 4.2 | 66.9 ± 4.6 |
| RR diast. Standing | 75.8 ± 5.4 | 77.3 ± 3.1 | 76.8 ± 3.7 | 78.4 ± 2.6 | 74.7 ± 4.3 | 74.8 ± 4.5 |
| Amplitude Lying Down | 39.7 ± 4.4 | $52.0^x \pm 5.9^o$ | 38.3 ± 5.1 | $47.3^o \pm 6.8$ | 39.0 ± 3.7 | 39.3 ± 4.4 |
| Amplitude Standing | 25.6 ± 5.8 | $39.3^x \pm 6.9^o$ | 24.6 ± 6.6 | $34.0^o \pm 7.6$ | 24.2 ± 3.9 | 25.1 ± 4.1 |

The use of the aforementioned combination resulted in an increase of the systolic blood pressure in the horizontal position by 15.1 mm Hg, while with etilefrin a rise of 11.1 mm Hg was recorded. In the case of the placebo the systolic blood pressure is 106 mm Hg both before and after the treatment. As with the use of the combination of etilefrin and horse chestnut seed extract the diastolic blood pressure again varies very little during the treatment, while the rise in the systolic blood pressure and the blood pressure amplitude in the course of the treatment demonstrates the desired increase of the cardiac output.

While the invention has been described in terms of various preferred embodiments, one skilled in the art will appreciate that various modifications, substitutions, omissions, and changes may be made without departing from the spirit thereof. Accordingly, it is intended that the scope of the present invention be limited solely by the scope of the following claims.

What is claimed is:

1. A method for the long term treatment of a mammal suffering from migraine comprising administering to the mammal a cardiac output increasing effective amount of etilefrin pivalate.

2. The method of claim 1 wherein the amount of etilefrin pivalate administered is less than about 0.8 per kg of body weight per day.

3. The method of claim 2 wherein the amount is between about 0.1 mg and about 0.8 mg per kg of body weight per day.

* * * * *